Figure 1:
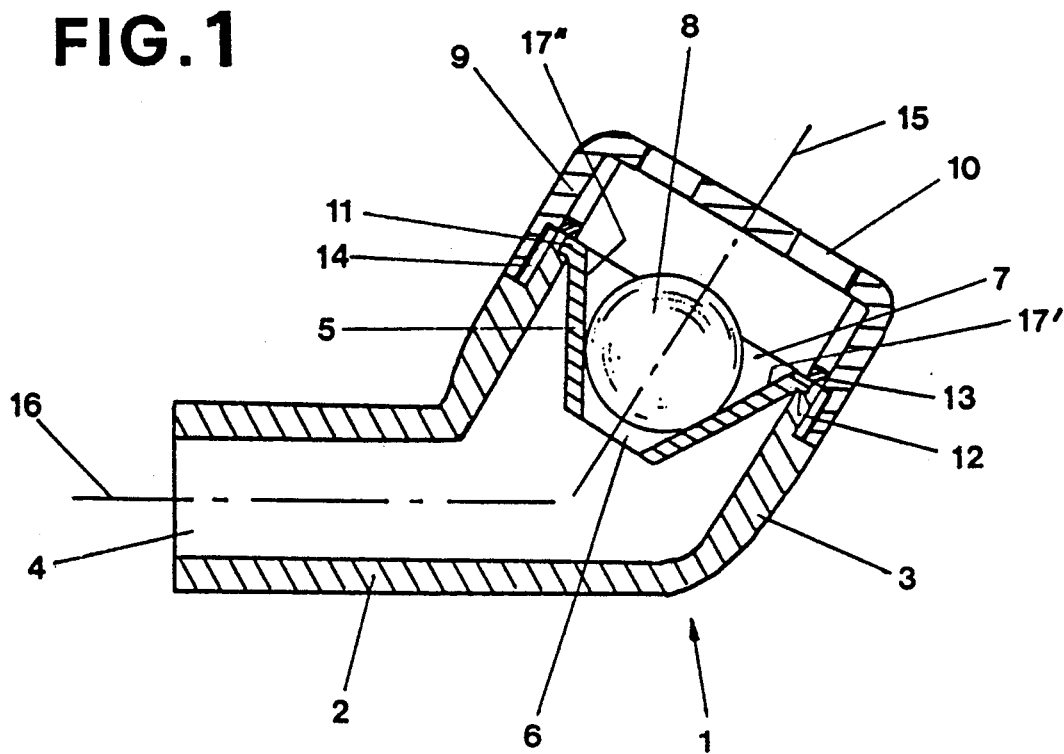

United States Patent [19]

Liardet

[11] Patent Number: 5,018,517
[45] Date of Patent: May 28, 1991

[54] EXPIRATION-RESISTING APPARATUS DESIGNED FOR IMPROVING PULMONARY VENTILATION

[76] Inventor: Claude Liardet, 30, rue Trévelin, CH-1170 Aubonne, Switzerland

[21] Appl. No.: 381,636
[22] PCT Filed: Oct. 22, 1987
[86] PCT No.: PCT/CH87/00146
§ 371 Date: Jun. 21, 1989
§ 102(e) Date: Jun. 21, 1989
[87] PCT Pub. No.: WO89/03707
PCT Pub. Date: May 5, 1989

[51] Int. Cl.[5] .............................. A63B 23/00
[52] U.S. Cl. ..................... 128/200.24; 272/99; 128/202.13
[58] Field of Search .......... 128/201.11, 207.16, 128/205.24, 201.13, 201.18, 200.24, 202.13, 202.16, 202.17, 204.18, 204.26, 204.27, 207.14, 207.15; 272/99

[56] References Cited

U.S. PATENT DOCUMENTS

| 737,008 | 10/1902 | Nichol | 272/99 |
| 3,908,987 | 9/1975 | Boehringer | 272/99 |
| 4,232,683 | 11/1980 | Bartholomew et al. | 272/99 |
| 4,275,722 | 6/1981 | Sorevsen | 128/203.12 |
| 4,403,615 | 9/1983 | King | 272/99 |

FOREIGN PATENT DOCUMENTS 86259369 12/1986 Fed. Rep. of Germany.
2236527 2/1975 France.

Primary Examiner—Clifford D. Crowder
Assistant Examiner—Lisa E. Malvad
Attorney, Agent, or Firm—Woodard, Emhardt, Naughton, Moriary & McNett

[57] ABSTRACT

The apparatus comprises a first tubular part (2) comprising an air inlet (4) wherein the patient may breathe out and a second part (3) comprising a conical channel (5) of which the axis (15) is inclined upwardly by an angle of 60° with respect to the axis (16) of the first tubular part. A steel ball (8) is arranged in the conical channel (5) so as to occlude said channel before expiration. During expiration, the ball is displaced along the lowest portion (17') of the channel and induces oscillating effects of resistance to expiration and allows a percussion ventilation of high efficiency. The apparatus further comprises a cover (9) presenting openings (10) and intended to prevent the ball from escaping.

9 Claims, 2 Drawing Sheets

EXPIRATION-RESISTING APPARATUS DESIGNED FOR IMPROVING PULMONARY VENTILATION

The present invention relates to an expiration-resisting apparatus designed for improving pulmonary ventilation.

Various apparatus are known which are intended for a specific therapy in the respiratory field, by improving the peripheral ventilation of invalids having a respiration which is disturbed for various causes, such as, for example, chronic bronchitis, asthma, problems as regards compliance, inadequate ratio of the pleural pressure with respect to the alveolar pressure, secondary infection, hypersecretion and mucous blockages, etc. These apparatus are used with success, but they are, however, all of a complex design, generally very cumbersome and very costly.

Apparatus of small dimensions have already been developed, which comprise a horizontal air passage connected to a vertical air passage comprising an outlet orifice, a movable element being so disposed as to obstruct the outlet orifice prior to expiration and to oppose a resistance to the expiration under the action of a resilient member or due to the effect of its own weight. In particular, an apparatus has been developed in which a heavy ball is disposed in the exhaust passage in the form of a vertical funnel, the ball, free to be displaced vertically, being lifted from its support at the time of expiration and offering a resistance to the expiration by the effect of its own weight. However, the results obtained with this apparatus are not as good as those obtained with the aforementioned more complex apparatus. Clinical tests have particularly shown that the percussion effect obtained with this type of apparatus remains small and is difficult to control.

The object of the invention is to propose an apparatus which permits of obtaining results equivalent to those obtained with the apparatus of more complex design and which is of small dimensions, is simple and less costly and which can easily be carried, for example, in a pocket.

To this end, the expiration-resisting apparatus in accordance with the invention has the features which are specified in claim 1. Features corresponding to particular embodiments of the resistance apparatus are set out in the claims which are subordinate to claim 1.

Studies and clinical tests which have been conducted have made it possible to show the importance of the inclination of the axis of the conical passage, so as, to form, firstly, a bed for the displacement of the ball and, secondly, an obstacle to this displacement, so as to obstruct the passage, thus enabling the ball to maintain a permanent contact with its support and to obtain a percussion effect which is appreciably increased with respect to the effect obtained with the apparatus which have been described above, while aiming for a low frequency.

Figure 2:
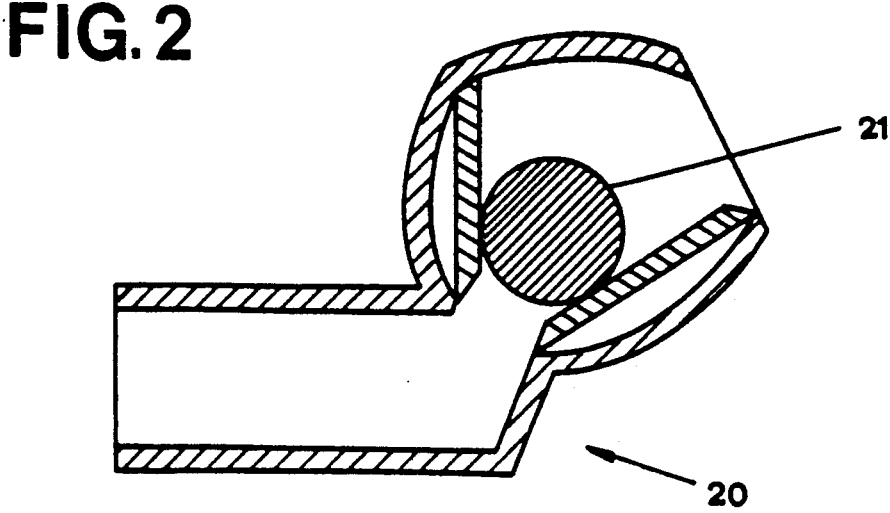
Figure 3A:
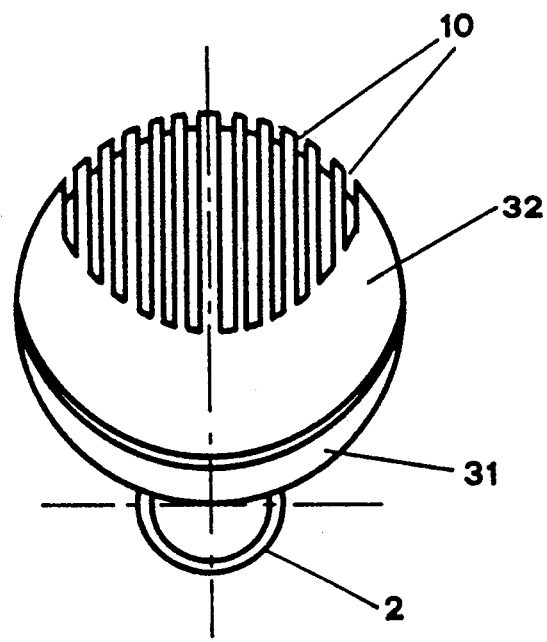
Figure 3B:
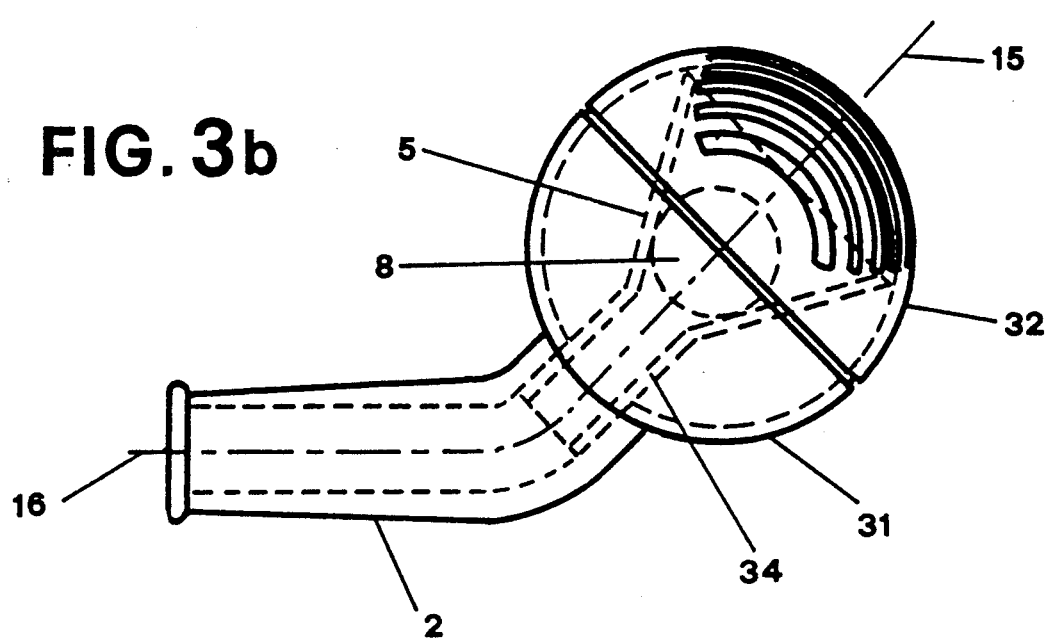

Other advantages and favourable characteristics of the expiration-resisting apparatus according to the invention will become more clearly apparent from the following description, given as an example and with reference to the accompanying drawing, wherein:

FIG. 1 is a vertical section of a first example of an expiration-resisting apparatus, FIG. 2 is a vertical section of a second example of an expiration-resisting apparatus, and FIG. 3 shows a third example of a resisting apparatus, seen from the front in FIG. 3a and from the side in FIG. 3b.

As shown in FIG. 1, the apparatus comprises a first element in the form of a bent cylindrical tube 1, open at its two ends, comprising a first rectilinear tubular part 2 intended to be held in a horizontal position and a second tubular part 3 which is inclined upwardly relatively to the first part. The first tubular part 2 comprises an air inlet orifice 4, into which the patient is able to expirate. A conical element 5, of which the walls have the form of a truncated right cone of revolution, is disposed within the second tubular part 3, so that its end of larger diameter 7 is located at the level of the end of the second tubular part 3, the end of smaller diameter 6 of the conical element being disposed within the tubular element. A ball 8, having a diameter which is larger than the smallest diameter 6 of the conical element is simply positioned against the internal wall of the conical element and completely obstructs the passage formed by the conical element, before the patient breathes out. The apparatus also comprises a cover 9, which is disposed at the end of the second tubular part 3 and has for its purpose to prevent the ball 8 from becoming loose. In order to permit the air which is expired to escape from the apparatus, the cover comprises one or more openings 10 which are shaped so as to prevent the passing through of the ball. The fixing of the cover 9 on the tubular element is effected by a bayonet-type device 14. It is obvious that this fixing arrangement may be replaced by a clip-type device or it may be designed so that the cover is screwed on to the tubular element.

The conical element 5 is removably secured in the apparatus. For this purposes, it comprises an external rim 11 situated on the circumference of its end of larger diameter, the said rim being adapted to be lodged in a corresponding notch 12 formed on the circumference of the internal wall of the end of the tubular element. The locking of the conical element in position is effected at the time of positioning the cover, due to the action of a member 13 in the form of a rim, which projects into the interior of the cover over its entire circumference and which bears against the larger diameter end of the conical element. The dismantlable structural design of the apparatus, which is able to be easily separated into four parts, namely, the bent tubular element, the conical element, the cover and the ball, permits efficient cleaning of the apparatus and the use thereof under best possible conditions as regards hygiene.

In order to obtain the desired percussion effect at the time of expiration of the patient, it is necessary to avoid the ball from lifting and floating above its support, but for said ball to remain in contact with the latter. This feature is obtained by the upward inclination at an angle smaller than 90° of the axis 15 of the conical element with respect to the axis 16 of the first part 2 of the bent tubular element. In addition, the opening angle of the conical element has to be so chosen that the angle formed by a generatrix 17' or 17" of the wall of the passage and the axis 15 of the said passage is smaller than the angle of inclination of the passage axis relatively to the axis 16 of the first tubular part 2. In this way, the ball is to be displaced by rolling on the internal wall of the conical element, the lowest part of the said wall 17' forming a rolling bed for the ball, the highest part of the said wall 17" forming a stop to the movement of the ball. When the first part 2 of the tubular element is held in a horizontal position by the patient, before expiration, the ball obstructs the conical passage by the effect of gravity due to its weight. At the time of expiration, the instantaneous position of the ball results from a state of equilibrium between the pressure of the air expired by the patient and the force of gravity due to the weight of the ball. The damping characteristic of the ball being very weak, what follows is an oscillatory movement of this latter, generating a variable pressure which opposes the expiration, by constituting a positive oscillating resistance to the expiration.

Experience has shown that this apparatus permits a ventilation in percussion with a high efficiency, secretions being mobilised in a few minutes in the bronchial tree of the patient, permitting the easy expectoration thereof. Best results are obtained with an expiration which is slow and as complete as possible. Measurements by oesophagal balloons have shown that the percussion phenomenon reaches the peripheral level of the lung. In addition to its very low cost, this apparatus has the great advantage of being able to be carried easily in the pocket of the patient during all his movements. Its use by way of training constitutes a very good respiratory exercise.

The best results are obtained with an apparatus in which the inclination of the axis 15 of the conical passage with respect to the axis 16 of the first part 2 of the tubular element is between 50° and 70°, and by using an element in the form of a truncated cone, of which the slope of the wall 17' (or 17") of the cone forms an angle which is between 20° and 30°, relatively to the axis 15 of the said cone. In particular, excellent results are obtained with an apparatus of which the axis 15 of the cone element is inclined by 60° in an upward direction with respect to the axis 16 of the first part 2 of the tubular element, the angle formed by the direction of the wall 17' (or 17") of the said conical passage with its axis 15 being 30°. In one preferred constructional form of the apparatus, the tubular element 1, the cone element 5 and the cover 9 are made by moulding from plastics material. Preferably stainless steel balls having a diameter which is between 16 and 25 millimeters are used. In this case, the length of the conical passage should be at least 1 centimeter and the diameter of its smallest end at least 1 centimeter. In order to enable the apparatus to function satisfactorily, the section of the air outlet orifice or orifices 10 should be equal to or larger than the entry section 6 of the cone element.

Obviously the apparatus also functions with other dimensions and when using other materials for its components, provided that the weight of the ball is sufficient for obtaining the desired percussion effect.

The clinical tests conducted with this resistance apparatus have made it possible for the following phenomena to be proved:

a position linear resistance to the expiration, adapted to the known therapeutic values, a percussive resistance (difference of pressure (ΔP) of the order of 5 to 10 centimeters of water) and of low frequency (about 10 to 20ΔP per second) adapted to the known therapeutic values, i.e. corresponding to the intrathothic values of an average "clapping".

These studies have also shown that this apparatus permits an automatic regulation at the same time of the positive linear pressure, of the percussion (ΔP) and of the frequency of this percussion, this regulation being inherent in the system and independent of the rate of flow of air.

Represented in FIG. 2 is a second constructional example of the resistance apparatus. This apparatus 20 is likewise made of a plastics material and comprises a detachable part (not shown) for permitting the introduction of the ball 21.

A third constructional example of the resistance apparatus is shown in FIG. 3. The first tubular part 2 of this apparatus is bent at its end opposite to the entry orifice and is surmounted by a part 31 in the form of a hemisphere, comprising a circular opening at its base, permitting communication with the passage of the first tubular part 2. The conical passage element 5 is extended at its base by a cylindrical tubular part 34, which is to be fitted into the passage of the first tubular part 2. A cover 32 of hemispherical form comprising openings 10 permits the apparatus to be closed and the escape of the ball 8 to be prevented.

It is obvious that the numerous embodiments may be envisaged, particularly as regards the aesthetic appearance of the apparatus. It is possible to provide this apparatus with an external form which has the imprint of one or several fingers, to enable the apparatus to be conveniently held in the hand.

I claim:

1. Expiration-resisting apparatus designed for improving pulmonary ventilation, characterized in that it comprises a first tubular part comprising an air inlet orifice into which the patient is able to expirate, and a second part comprising an exhaust passage of circular conical form, the axis of the said passage being inclined upwardly with respect to the axis of the part of tubular form at an angle of inclination comprised between 30° and 80°, the angle formed by a generatrix of the wall of the passage and the axis of the passage being smaller than the angle of inclination of the passage axis, a spherical ball o a diameter larger than the smallest diameter of the conical passage of the conical passage being disposed in the said passage so as to obstruct the said passage prior to expiration, the ball being able to be displaced freely in the said passage and offering a resistance to the expiration of the air exhaled by the patient by the effect of its own weight, the apparatus being so shaped as to permit the expired air to escape through at least one hole disposed in a zone opposite to the entry orifice of the conical passage, the dimensions of the hole being chosen so as to prevent the escape of the ball.

2. Apparatus according to claim 1, characterized in that the angle formed by a generatrix of the wall of the conical passage and the axis of the passage is between 20° and 35°.

3. Apparatus according to claim 1, characterized in that the inclination of the axis of the conical passage relatively to the axis of the first part of tubular form is 60°, the angle formed by a generatrix of the wall of the passage and the axis of the passage being 30°.

4. Apparatus according to claim 2, characterized in that the angle formed by a generatrix of the wall of the conical passage and the axis of the passage is between 20° and 35°.

5. Apparatus according to one of the preceding claims, characterized in that it comprises a bent element of tubular form which is opened at its two ends, the first end constituting the air inlet orifice into which the patient is able to expirate, a cover element comprising at least one opening being removably fixed to the second end of the bent element, the conical passage being formed by an element in the form of a truncated cone, also fixed so as to be removable to the second end of the bent element, the end of smaller diameter of the cone element being located within the bent element.

6. Apparatus according to claim 5, characterized in that the ball is made of steel, its diameter being between 16 and 25 millimeters.

7. Apparatus according to claim 6, characterized in that the length of the conical passage is at least 1 centimeter, the diameter of its smallest end being at least 1 centimeter.

8. Apparatus according to claim 1, characterized in that the length of the conical passage is at least 1 centimeter, the diameter of its smallest end being at least 1 centimeter.

9. Apparatus according to claim 1, characterized in that the ball is made of steel, its diameter being between 16 and 25 millimeters.

* * * * *

UNITED STATES PATENT AND TRADEMARK OFFICE
CERTIFICATE OF CORRECTION

PATENT NO.   : 5,018,517
DATED        : May 28, 1991
INVENTOR(S)  : Claude Liardet It is certified that error appears in the above-identified patent and that said Letters Patent is hereby corrected as shown below:

ON TITLE PAGE:

In the name of the Attorney, Agent, or Firm
    line 2, please delete "Moriary" and insert in lieu thereof
--Moriarty--.

In column 4, line 36, between the words "ball" and "a" please delete the letter "o" and insert in lieu thereof the word --of--.

Signed and Sealed this

Twenty-ninth Day of September, 1992

Attest:

DOUGLAS B. COMER

*Attesting Officer*         *Acting Commissioner of Patents and Trademarks*